US008129359B2

United States Patent
Herzberg et al.

(10) Patent No.: US 8,129,359 B2
(45) Date of Patent: Mar. 6, 2012

(54) COMPOSITION AND METHOD FOR TREATING POST-SURGICAL PAIN

(75) Inventors: Uri Herzberg, Bridgewater, NJ (US); Robert A. Rousseau, Ottsville, PA (US); J. Jenny Yuan, Branchburg, NJ (US); Dwayne Looney, Flemington, NJ (US); Hock S Tan, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 1270 days.

(21) Appl. No.: 10/861,632

(22) Filed: Jun. 4, 2004

(65) Prior Publication Data

US 2005/0272697 A1 Dec. 8, 2005

(51) Int. Cl.
*A61K 31/717* (2006.01)
*A61K 31/715* (2006.01)
(52) U.S. Cl. ................. 514/57; 514/54; 536/57; 536/56
(58) Field of Classification Search .................... 514/57, 514/54; 536/57, 56
See application file for complete search history.

(56) References Cited

U.S. PATENT DOCUMENTS 3,364,200 A    1/1968  Ashton et al.
(Continued)

FOREIGN PATENT DOCUMENTS

EP    0274870 A    7/1988
(Continued)

OTHER PUBLICATIONS

Brennan, T. J. et al. "Characterization of a rat model of Incisional pain", Pain, 64 (1996): 493-501.

(Continued)

*Primary Examiner* — Shaojia Anna Jiang
*Assistant Examiner* — Michael C Henry
(74) *Attorney, Agent, or Firm* — Roberts Mlotkowski Safran & Cole, P.C.

(57) ABSTRACT

A composition for reducing pain at a surgical wound site or trauma site comprising oxidized regenerated cellulose and a non-steroidal anti-inflammatory drug or pharmaceutically acceptable salt or ester thereof, where the non-steroidal anti-inflammatory drug is an acid having a secondary amine group; and a method of reducing localized pain at a surgical wound site or trauma site.

21 Claims, 4 Drawing Sheets

U.S. PATENT DOCUMENTS

| | | | |
|---|---|---|---|
| 4,937,254 | A | 6/1990 | Sheffield et al. |
| 5,180,398 | A | 1/1993 | Boardman et al. |
| 5,565,210 | A * | 10/1996 | Rosenthal et al. ............ 424/426 |
| 5,888,523 | A | 3/1999 | Galask et al. |
| 6,159,955 | A | 12/2000 | Asculai et al. |
| 6,197,822 | B1 | 3/2001 | Hammond |
| 6,231,888 | B1 | 5/2001 | Lerner et al. |
| 6,242,010 | B1 * | 6/2001 | Hersh ............................ 424/702 |
| 6,548,501 | B2 | 4/2003 | Hakkinen |
| 6,689,382 | B2 | 2/2004 | Berthel et al. |
| 6,723,314 | B2 | 4/2004 | Keith, Jr. et al. |
| 2002/0188005 | A1 | 12/2002 | Farrar et al. |
| 2003/0118651 | A1 | 6/2003 | Jampani et al. |
| 2004/0001879 | A1 | 1/2004 | Guo et al. |
| 2004/0022837 | A1 | 2/2004 | Hsu et al. |

FOREIGN PATENT DOCUMENTS

| | | |
|---|---|---|
| EP | 0 485 111 | 5/1992 |
| EP | WO 98/43477 | 10/1998 |
| EP | 0 896 822 | 2/1999 |
| EP | 1 027 891 | 8/2000 |
| EP | 1405646 A2 * | 4/2004 |
| WO | WO 02/34240 A | 5/2002 |
| WO | WO 2004/026200 A | 4/2004 |
| WO | WO 2004/112850 A | 12/2004 |
| WO | WO 2005/049101 A | 6/2005 |

OTHER PUBLICATIONS

Chaplan et al., J. Neurosci. Methods 1994, 53: 55-63.

Vuori A: Salo M; Viljanto J.; Pajulo O Pulkki K; Nevalainen T: "Effects of Post-Operative Pain Treatment Using Non-Steriodal Anti-Inflammatory Angalgesics, Opiods or Epidural Blockade on Systemic and Local Immune Responses in Children" ACTA Anaesthesiollogica Scandinavica, vol. 48, No. 5, Jul. 2004, pp. 738-749, XP008055633.

International Search Report dated Nov. 24, 2005 for corresponding Appln. No. PCT/US2005/018694.

Fabio A. Kudo, Toshiya Nishibe, Keiko Miyasaki, Toshifumi Murashita, Masayasu Nishibe and Keishu Yasuda, "Use of Bioresorbable Membrane to Prevent Postoperative Small Bowel Obstruction in Transabdominal Aortic Aneurysm Surgery", Dept. of Cardiovascular Surgery,, Hokkaido University School of Medicine, Sappaoro, Japan et al, Surg Today (2004) 34:648-651.

Roman P. Korolkiewica M.D., Phd., Marek UJDA, M.D. Jaroslaw Dabkowski, M.D., Jaroslaw Ruczynski, M.Sc., Piotr Rekowski, Ph.D. and Jacek Petrusewicz, Ph.D., "Differential Salutary Effects of Nonselective and Selective COS-2 Inhibitors in Postoperative ileus in Rats", Dept. of Pharmacology, Medical University of Gdarisk, Do Studzienski 38, 80-227 Gdansk, Poland et al., Journal of Surgical Research (2003)109, 161-169.

Makoto Kadowaki, Yasunori Nagakura, Kenichi Tokita, Kaori Hanaoka, Masaaki Tomoi "Adenosine A1 receptor blockade reverses experimental postoperative ileus in rat colon", Pharmacological Research Laboratories, Fujisawa Pharmaceutical Co., Ltd. Osaka 532-0031, Japan, European Journal of pharmacology (2003)458: 197-200.

Benedicte Y. De Winter, Guy E. Boeckxstanens, Joris G. De Man, Tom G. Moreels, Arnold G. Herman, and Paul A. Pelckmans, "Effect of adrenergic and nitrergic blockade on experimental ileus in rats" Div. of Gastroenterology and Pharmacology, Faculty of Medicine, University of Antwerp, Universiteitsplein 1, 2610 Antwerp, Belgium et al., British Journal of Pharmacology (1997)120; 464-468.

Brady et al: Analgesic Effects of Intraventricular Morphine and Enkephalins in Nondependent and Morphine-Dependent Rats; The J. of Pharmacology & Experimental Therapeutics. Apr. 12, 1982; pp. 190-197; vol. 222, No. 1; ASPET; USA.

N. Shafiq, S. Malhotra and P. Pandhi, "Effect of Cyclooxygenase Inhibitors in Postoperative Ileus: An Experimental Study", Dept. of Pharmacology, Postgraduate Institute of Medical Education and Research, Chandigarh, India, Methods Find Exp Clin Pharmacol (2002)24(5): 275-278.

* cited by examiner

Tissue Concentration of DCF-Na.

FIG. 3B

Plasma Concentration of DCF-Na.

COMPOSITION AND METHOD FOR TREATING POST-SURGICAL PAIN

BACKGROUND OF THE INVENTION

This invention is generally in the field of anesthesiology and, in particular, the non-systemic or localized administration of non-steroidal anti-inflammatory drugs to traumatized tissue for the treatment of localized pain.

Pain can be defined as an unpleasant sensory and emotional experience associated with actual or potential tissue damage. It is a complex process influenced by both physiological and psychological factors. Pain is typically subjective and many health care professionals are not trained to effectively assess or treat pain. The management of pain, particularly post-surgical pain, is most often based on the systemic administration of pain relieving drugs.

The three major classes of pharmaceutical drugs used to treat post-surgical pain are the opiates, local anesthetics, and the non-steroidal anti-inflammatory drugs (NSAID). Two of these classes of drugs, the opiates and NSAIDs, are typically administered systemically while the local anesthetics (e.g. channel blockers) are administered non-systemically during surgery. The systemic administration of drugs to relieve pain after surgery is frequently inadequate. For example, systemic administration of opiates after surgery may cause nausea, the inhibition of bowel function, urinary retention, inhibition of pulmonary function, cardiovascular effects, and sedation. When NSAIDs are given systemically, there is a potential for gastrointestinal (GI) and renal side effects as well as inhibition of platelet function.

The effectiveness of NSAIDs on traumatized tissue during the inflammatory period of wound healing combined with their "opiate sparing" ability and weak central analgesic effect make them ideal potential candidates for non-systemic or localized administration to traumatized tissue for the reduction of localized pain, as recognized for example in US 2003/0118651. As used herein, the term "non-systemic" refers to the application of a composition or drug to the site of a traumatized tissue, intracorporeally at a surgical wound site or a trauma site, or topically, i.e., internally and/or externally. The terms "surgical wound site" and "trauma site" are meant to include the site of tissue that has been injured in any way, and includes, for example, tissue sites that have undergone incision, drying, suturing, excision, abrasion, contusion, laceration, anastomosis, manipulation, prosthetic surgery, curettage, orthopedic surgery, neurosurgery, cardiovascular surgery, or plastic or reconstructive surgery. The treatment is intended to be "locally effective", that is the treatment is intended to affect only the tissue treated or adjacent or neighboring tissue.

There are numerous references generally describing the administration of NSAIDs via drug delivery systems that may be utilized non-systemically. The efficacy of various NSAIDs for the treatment of post-surgical pain are also reported in many of these references. These systems typically consist of a polymeric matrix or liposome from which drug is released by diffusion and/or degradation of the matrix. The release pattern is usually principally determined by the matrix material, as well as by the percent of loading, method of manufacture, type of drug being administered and type or geometry of the device. Often the drug delivery system is biocompatible and absorbable, which permits it to be used intracorporeally at the surgical wound site or trauma site and then slowly absorbed by the patient's body. One advantage of using an absorbable drug delivery system at the surgical wound site or trauma site is that the site does not have to be re-opened to remove the drug delivery system after depletion of the drug.

For example, U.S. Pat. No. 4,937,254 teaches that NSAIDs can be administered non-systemically and intercorporeally to a surgical wound site or trauma site via incorporation of the NSAID and a pharmaceutically acceptable carrier such as hyaluronic acid, chitosan, and liposome, directly at the site of the traumatized tissue. Examples of the NSAID include ibuprofen, suprofen or tolmetin. This reference describes the efficacy of such NSAIDs for inhibiting post-surgical adhesions, but not for reducing post-surgical localized pain.

U.S. Pat. No. 5,888,523 describes a NSAID composition that may be used for the non-systemic treatment of pain associated with inflamed/irritated tissue. Specifically, this reference is directed to the use of an aqueous based carrier system for NSAIDs for topical application on the inflamed/irritated tissue. In particular, the system described in this reference consists of a water dispersible natural cellulosic polymer, an organic acid, and an NSAID. This reference specifically reports the efficacy of naproxen and ibuprofen for the treatment pain associated with vulvodynia or vulvar vestibulitis, and suggests that drugs such as indomethacin, diclofenac and ketoprofen may also be used. This reference does not describe, suggest or predict the efficacy of the NSAID system when used intracorporeally at a surgical wound site or trauma site for the non-systemic treatment of localized pain associated therewith.

Although the prior art reports the efficacy of a naproxen or ibuprofen system for the treatment pain associated with vulvodynia or vulvar vestibulitis (via topical application), and suggests that systems containing drugs such as indomethacin, diclofenac and ketoprofen are efficacious for the treatment pain associated with vulvodynia or vulvar vestibulitis (via topical application) in U.S. Pat. No. 5,888,523; such results and suggestions are not predictive of the efficacy of, for example, an indomethacin, diclofenac or ketoprofen system when administered non-systemically and intercorporeally at the site of a surgical wound or trauma, for the reduction of localized pain at the site. As the clinical requirement for a drug delivery carrier of any given therapeutic agent for intercorporeal application at a surgical wound site or a trauma site is much more demanding than for topical application of the same therapeutic agent, there is usually no predictive correlation between non-systemic topical application and non-systemic intercorporeal application at a surgical wound site or a trauma site of a particular NSAID system. In addition to drug-carrier compatibility, critical factors to consider for a drug delivery carrier for use in intercorporeal application at a surgical wound site or a trauma site include, but is not limited to, tissue reaction, biocompatibility, bioabsorbability, biodegradability, and mechanical strength. For example, one would not expect the mechanical properties of the NSAID composition disclosed in U.S. Pat. No. 5,888,523 to be suitable for intercorporeal use at a surgical wound site or a trauma site, because the NSAID composition is based on a water dispersible cellulosic polymer that is not expected to remain in the fluid environment of the body for a long enough period of time to allow for release of the NSAID. Additionally, according to the material safety data sheet (MSDS), small organic acids such as citric acid, acetic acid, maleic acid and lactic acids may cause undesired health hazards, for instance, skin irritation, respiratory tract irritation, allergic reactions and mucos membrane burns. The presence of an organic acid in the NSAID composition renders its biologically incompatible with a surgical wound site or a trauma site, even possibly causing tissue irritation that may be detrimental to wound healing.

As described above, NSAID's are ideal potential candidates for non-systemic or localized administration to traumatized tissue for the reduction of localized pain. Therefore, it is desirable to have a NSAID drug delivery system that is efficacious when administered non-systemically and intercorporeally at the site of a surgical wound or trauma, for the reduction of localized pain at the site.

BRIEF SUMMARY OF THE INVENTION

One embodiment of the invention is directed to a composition for reducing pain at a surgical wound site or trauma site comprising oxidized regenerated cellulose and a NSAID or pharmaceutically acceptable salt or ester thereof, where the NSAID is an acid having a secondary amine group. In another embodiment, the NSAID is diclofenac or mefenamic acid.

Another embodiment of the invention is a medical device comprising a composition for reducing pain further comprising oxidized regenerated cellulose and a NSAID or pharmaceutically acceptable salt or ester thereof, where the NSAID is an acid having a secondary amine group. In another embodiment, the NSAID is diclofenac or mefenamic acid.

Another embodiment of the invention is directed to a method for reducing pain at a surgical wound site or trauma site including, applying to the site an effective amount of a composition containing oxidized regenerated cellulose and a NSAID or pharmaceutically acceptable salt or ester thereof, where the NSAID is an acid having a secondary amine group, to reduce localized pain at the site. In another embodiment, the NSAID is diclofenac or mefenamic acid.

The present invention relates to a biocompatible and absorbable composition useful for treating localized pain at a surgical wound site or trauma site. As used herein, "biocompatible" means that, once applied, the composition will not result in substantial tissue irritation or necrosis. The term "absorbable" means that the composition will be absorbed by the body over time by the action of enzymes, hydrolytic action or by contact with substances found in the surrounding tissue fluids or cellular action.

BRIEF DESCRIPTION OF THE INVENTION

DETAILED DESCRIPTION OF THE INVENTION

The non-systemic intercorporeal application of an oxidized regenerated cellulose—based NSAID system was evaluated by the present inventors. As will be described in more detail below, neither indomethacin nor ketoprofen is efficacious in the oxidized regenerated cellulose—based NSAID system for the reduction of pain at a surgical wound site, while diclofenanc exhibits surprisingly efficacious results. These results demonstrate the unpredictable nature of the analgesic effect of a drug delivery system when administered non-systemically and intercorporeally at the site of a surgical wound or trauma, for the reduction of localized pain at the site.

As a result of these evaluations, it has been discovered that a composition comprising oxidized regenerated cellulose and an effective amount of a NSAID or pharmaceutically acceptable salt or ester thereof to treat localized pain, where the NSAID is an acid having a secondary amine group, is surprisingly efficacious when administered non-systemically and intercorporeally at the site of a surgical wound or trauma, for the reduction of localized pain at the site. In particular, the non-steroidal anti-inflammatory drug is 2-((2,6-ichlorophenyl)amino)benzeneacetic acid (I) also referred to as diclofenac, or 2-[(2,6-dichlorophenyl)amino]-Benzeneacetic acid, monosodium salt (II), or 2-[(2,3-dimethylphenyl)amino]-benzoic acid (III), also referred to as mefenamic acid, which having the following structures I, II and III, respectively:

It is understood that the present invention contemplates the use of not only the above-stated NSAID compounds themselves, but their pro-drugs which metabolize to the compound and the analogues and biologically active salt forms thereof, as well as optical isomers which provide the same pharmaceutical results.

Oxidized regenerated cellulose and a detailed description of its method of manufacture is set forth in U.S. Pat. No. 3,364,200, which discloses the preparation of carboxylic-oxidized cellulose with an oxidizing agent such as dinitrogen tetraoxide in a Freon medium, and U.S. Pat. No. 5,180,398, which discloses the preparation of carboxylic-oxidized cellulose with an oxidizing agent such as nitrogen dioxide in a per-fluorocarbon solvent, the contents each of which is hereby incorporated by reference as if set forth in its entirety. After oxidation by either method, the carboxylic-oxidized cellulose is thoroughly washed with a solvent such as carbon tetrachloride, followed with an aqueous solution of 50 percent isopropyl alcohol (IPA), and finally with 99% IPA. As such, teachings concerning oxidized regenerated cellulose and methods of making the same are well within the knowledge of one skilled in the art.

The oxidized regenerated cellulose that may be used in one embodiment include fabrics utilized as conventional adhesion barriers or conventional hemostatic wound dressings, such as Interceed® absorbable adhesion barrier; Surgicel® absorbable hemostat; Surgicel Nu-Knit® absorbable hemostat; and Surgicel® Fibrillar absorbable hemostat; all available from Gynecare Worldwide or Johnson & Johnson Wound Management Worldwide, divisions of Ethicon, Inc., Somerville, N.J., a Johnson & Johnson Company; as well as Oxycel® absorbable cellulose surgical dressing from Becton Dickinson and Company, Morris Plains, N.J. Oxidized cellulose powder such as Curacel® oxidized regenerated cellulose powder from Curaspon Healthcare, the Netherlands, also may be used. The fabrics are characterized by having a single ply thickness of at least about 0.5 mm, a density of at least about 0.03 g/cm$^2$, air porosity of less than about 150 cm$^3$/sec/cm$^2$, and liquid absorption capacity of at least about 3 times the dry weight of the fabric and at least about 0.1 g water per cm2 of the fabric.

In the embodiment where a fabric or textile is utilized, a solution of the non-steroidal anti-inflammatory drug or a pharmaceutically acceptable salt or ester thereof may be incorporated into the composition by (a) dip coating the oxidized regenerated cellulose textile in a solution or suspension of the non-steroidal anti-inflammatory drug; (b) spray drying a solution or suspension of the non-steroidal anti-inflammatory drug onto the oxidized regenerated cellulose textile; (c) laminating at least one polymeric film formed from an aqueous, non-aqueous or organic solution or suspension of the non-steroidal anti-inflammatory drug onto the oxidized regenerated cellulose textile; or (d) forming a microporous polymeric matrix of non-steroidal anti-inflammatory drug onto an oxidized regenerated cellulose textile. Polymers that may be laminated onto the oxidized regenerated cellulose textile may be water-soluble polymers that include, but are not limited to, poly(acrylic acid), hydroxylpropyl methyl cellulose, polyvinyl pyrrolidone, polyethylene glycol, and polyethylene oxide. These polymers, used to accurately control the dosage or loading of non-steroidal anti-inflammatory drug onto the textile during processing, are fast dissolving in an aqueous environment. Since these polymers are fast dissolving intercorporeally, they do not cause any significant delay in the release of the non-steroidal anti-inflammatory drug, and the release profile of non-steroidal anti-inflammatory drug is controlled by oxidized regenerated cellulose textile. The microporous polymeric matrix of non-steroidal anti-inflammatory drug may be formed by incorporating the NSAID having the secondary amine group into the microporous polymeric matrix described in US 2004/0001879A1, which is incorporated herein by reference.

In addition to fabrics, the oxidized regenerated cellulose may be in the form of particles. For example, in one embodiment, oxidized regenerated cellulose textile may be micronized to particles having an average particles size of 1-1000 microns, and preferably of 20-25 microns, as measured by a Beckman Coulter Particle Size Analyzer [LS13320, Tornado Dry Powder System and Universal Liquid Module]. In this embodiment, the composition comprises oxidized regenerated cellulose particles and non-steroidal anti-inflammatory drug particles or a pharmaceutically acceptable salt or ester thereof having an average particle size of 1-1000 microns, and preferably 1-100 microns. For example, the oxidized regenerated cellulose powder may be blended with the NSAID powder for final use. To achieve a range of oxidized regenerated cellulose particle sizes to be used in a co-blended powder, oxidized regenerated cellulose may be subjected to, for example, cryogenic milling.

In other embodiments, the composition of the present invention may comprise oxidized regenerated cellulose particles; a porous binder component; and a NSAID or pharmaceutically acceptable salt or ester thereof, and may be in the form of a foam sponge, foam beads or agglomerates.

In one embodiment, oxidized regenerated cellulose textile may be micronized to particles having an average particles size of 1-1000 microns, and preferably of 20-25 microns, as measured by a Beckman Coulter Particle Size Analyzer [LS13320, Tornado Dry Powder System and Universal Liquid Module], may be used, as described below in Example 4.

In alternate embodiments, oxidized regenerated cellulose particles or short fibers utilized to make foam sponges, foam beads or agglomerates may have an average size ranging from about 500 to about 5000 microns, preferably from about 680 microns to about 4350 microns. Such oxidized regenerated cellulose particles may be made by chopping the oxidized regenerated cellulose fabrics described above or any oxidized regenerated cellulose textile with a cutting blade of a motor-driven mill to the desired fiber length using an Thomas-Wiley® Laboratory Mill, Intermediate Model cutting blade. The motor-driven mill, with two stationary blades and a motor with four cutting edges revolving at high speed to produce a shearing action, is ideal for rapid milling of fabric samples. For example, the oxidized regenerated cellulose particles may be made by placing an oxidized regenerated cellulose textile, such as Surgicel® absorbable hemostat; Surgicel Nu-Knit® absorbable hemostat; or Surgicel® Fibrillar absorbable hemostat, or an oxidized regenerated cellulose, in a stainless steel foil pouch filled with liquid nitrogen and submerging the foil pouch in liquid nitrogen. The foil pouch is then passed through a dual wheel roller at, for example, 6 in/min, yielding oxidized regenerated cellulose having an average particle size of 0.035-4.35 mm.

The oxidized regenerated cellulose used in the foam sponge, foam beads or agglomerates may be conditioned prior to use. Conditioning can be achieved by storing the oxidized regenerated cellulose at room temperature under ambient conditions for at least 6 month, or conditioning can be accelerated. Alternatively, the oxidized regenerated cellulose is exposed to conditions of about 4° C. to about 90° C., at a relative humidity of from about 5% to about 90%, for a time of from about 1 hour to 48 months; conditions of about 4° C. to about 60° C., at a relative humidity of from about 30% to about 90%, for a time of from about 72 hours to 48 months; conditions of about 18° C. to about 50° C., at a relative humidity of from about 60% to about 80%, for a time of from about 72 hours to 366 hours; or conditions of about 50° C., at a relative humidity of about 70%, for a time of about 168 hours.

As a result of the conditioning, the oxidized regenerated cellulose will comprise at least about 3 weight percent of water-soluble molecules, preferably from about 3 to about 30 weight percent, more preferably from about 8 to about 20 weight percent, even more preferably from about 9 to about 12 weight percent, and most preferably about 10 weight percent. In general, the water-soluble molecules are acid-substituted oligosaccharides containing approximately 5 or fewer saccharide rings.

In the embodiments where the composition is a foam sponge, foam beads or agglomerates, the oxidized regenerated cellulose also will comprise from about 3 to about 20 weight percent of water, preferably from about 7 to about 13 weight percent, and more preferably from about 9 to about 12 weight percent water prior to use. Similar levels of moisture and water-soluble molecules in the carboxylic-oxidized regenerated cellulose also may be achieved by other means. For example, sterilization by known techniques, such as gamma or e-beam irradiation, may provide similar content of water and/or water-soluble molecules. In addition, water-soluble molecules such as oligosacchrides could be added to the oxidized regenerated cellulose particles prior to use.

The polymer used to prepare the porous binder component in the foam sponge, foam beads or agglomerates is a biocompatible, water-soluble, or water-swellable polymer. The fluid-absorbing polymer, when in a dry or concentrated state, interacts with body fluid through a hydration process. Once applied to a surgical wound site or trauma site, the polymer interacts with the water component in the tissue fluids via the hydration process. A preferred weight ratio of polymer to oxidized regenerated cellulose is from about 1:99 to about 15:85. A more preferred weight ratio of polymer to oxidized regenerated cellulose is from about 3:97 to about 10:90.

Polymers that may be used as a binder component or to form the microporous polymeric matrix of non-steroidal anti-inflammatory drug onto a oxidized regenerated cellulose textile (as described in (d) above), include but are not limited to, polysaccharides and proteins. Such polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of proteins include, but are not limited to, collagen and gelatin.

The foam sponge, foam beads or agglomerates may be made by first dissolving at least one water-soluble or water-swellable polymer in water to make a polymer solution. The non-steroidal anti-inflammatory drug may be dissolved or suspended in the polymer solution to form a solution or dispersion. The oxidized regenerated cellulose particles and the polymer solution/dispersion having the NSAID may then be homogenized using an Ultra-TURRAX® T18 DIXI midi Dispersers/Homogenizers to aid the dispersion of particles throughout the solution. The homogenizer, with its mechanical action, is known for use in blending unlike materials to make a homogenous distribution. After the oxidized regenerated cellulose particles are dispersed in the polymer solution having the NSAID, the dispersion is subjected to conditions under which the dissolved water-soluble or water-swellable polymer is solidified so as to provide a porous binder component for the oxidized regenerated cellulose particles and the NSAID. The solvent, i.e. water, may then be extracted from the composition to yield a porous composition comprising the oxidized regenerated cellulose particles of desired size, the porous binder component and the NSAID.

Depending on the conditions to which the homogenous dispersion is subjected, the compositions may be in various forms. For example, the compositions may be in the form of a porous foam, whereby the oxidized regenerated cellulose particles and the NSAID are dispersed in a porous binder component to form a porous foam sponge or porous foam beads, depending on the methods used to prepare the composition. In such cases, the oxidized regenerated cellulose particles and the NSAID may be bound within the structure of the porous binder component. At the same time, the porous nature of the binder component allows greater exposure of the binder to water within the body. The compositions also may take the form of a porous agglomerate of oxidized regenerated cellulose particles, NSAID and polymer binder. In such a case, the porous binder component may take on a more fibrous structure that is intertwined with the oxidized regenerated cellulose particles and NSAID, as opposed to a foam structure of the sponge or beads. Again, the porous nature of the agglomerates, due in part to the fibrous structure of the porous binder component, permits greater exposure of the polymer binder to the water in the body. In both cases, the surface area of the binder is maximized so as to provide faster and more extensive hydration by water in the body.

One method of making the porous foam sponge is to dissolve at least one water-soluble or water-swellable polymer in an appropriate solvent for the polymer to prepare a homogenous polymer solution; dissolve or suspend the non-steroidal anti-inflammatory drug in the polymer solution; contact the oxidized regenerated cellulose particles with an appropriate amount of the homogeneous polymer solution having the NSAID, such that the oxidized regenerated cellulose particles are dispersed in the polymer solution having the NSAID; and then flash-freeze the polymer solution having the particles/NSAID and dry/remove the solvent from the frozen structure by, for example, lyophilization at a pressure ranging preferably from 0-250 mtorr, more preferably from 0-200 mtorr, at a temperature ranging from 0C to −50° C., for a time duration ranging from 10-14 hours. Lyophilization removes the solvent by sublimation, leaving a porous foam sponge having the oxidized regenerated cellulose particles and NSAID dispersed throughout the porous binder component. NSAID is dispersed with the oxidized regenerated cellulose particles throughout the porous binder component in the foam sponge. The porous foam sponge, comprising oxidized regenerated cellulose particles, a binder component, and a NSAID or pharmaceutically acceptable salt or ester thereof, may further comprise a textile for additional reinforcement.

The advantages of freeze-drying can be summarized as follows: The drying at low temperatures reduces degradation of heat-sensitive products; the liquid product can be accurately dosed; the moisture content of the final product can be controlled during the process; the dry product can have an appealing physical form; and the dry product with a high specific surface area is rapidly reconstituted. The type of microporous morphology developed during the freeze-drying (lyophilization) is a function of several factors, such as the solution thermodynamics, freezing rate, temperature at which it is frozen, and concentration of the solution.

To maximize surface area, porous foam beads may be made, where the homogenized polymer solution/particles/NSAID may first be quickly frozen at lower than 0° C., preferably at about −50° C., i.e. by dripping the solution into liquid nitrogen, followed by removal of the solvent at a pressure ranging preferably from 0-250 mtorr, more preferably from 0-200 mtorr, at a temperature ranging from 0° C. to −50° C., for a time duration ranging from 10-14 hours; leaving porous foam beads having the oxidized regenerated cellulose particles and NSAID dispersed throughout the porous binder component.

One method of making the porous fibrous agglomerates of the present invention is to dissolve the water-soluble or water-swellable polymer in an appropriate solvent for the polymer to prepare a homogenous polymer solution; dissolve or suspend the non-steroidal anti-inflammatory drug in the polymer solution; contact the oxidized regenerated cellulose particles with an appropriate amount of the polymer solution having the NSAID by homogenization, such that the oxidized regenerated cellulose particles are dispersed in the polymer solution having the NSAID; dripping the homogenized dispersion into isopropanol to precipitate the water-soluble or water-swellable polymer and to form fibrous agglomerates having oxidized regenerated cellulose dispersed therein, and then flash-freeze and dry/remove the solvent from the fibrous agglomerates by, for example, lyophilization at a pressure ranging preferably from 0-250 mtorr, more preferably from 0-200 mtorr, at a temperature ranging from 0° C. to −50° C., for a time duration ranging from 10-14 hours, leaving porous agglomerates having the oxidized regenerated cellulose particles and NSAID dispersed throughout a fibrous structure of porous binder component.

In addition, the composition of the present invention may be prepared by compacting the porous foam beads or fibrous agglomerates such as may be practiced in producing non-woven felt fabrics. Foam beads or fibrous agglomerates may be made to such a size as to permit the formation of pastes or slurries comprising the beads or agglomerates, whereby the pastes or slurries may be applied to or injected into areas requiring pain treatment. Such pastes and slurries are reported in the art and once having the benefit of this disclosure those skilled in the art would readily be able to prepare such devices. Other embodiments contemplated by the inventors include a powder, a patch, or a plug whereby beads or agglomerates are compressed or formulated with excipients.

If the relief of pain is insufficient with NSAIDs alone, anesthetic agents like sodium channel blockers may be added to the composition. Because these two classes of drugs exert their effects by different mechanisms, combinations of these two classes of drugs may achieve an analgesic effect that would otherwise require a higher dose of sodium channel blocker, but with fewer side effects. Alternatively, atypical opiates such as loperamide or tramadol may also be added to the composition.

The composition may also benefit from having a variety of substances included such as stabilizers, wetting agents, or preservatives. Other drugs may also be added to the composition, so long as it is compatible with the NSAID and the remaining ingredients. These drugs include antibiotics, anti-viral, and anti-fungal agents. Since tissue sites are occasionally infected, an antibiotic or anti-microbial agent may also be combined with the composition.

When brought in contact with fluids in the body, such as blood, cerebrospinal fluid, or peritoneal fluid, the composition of the present invention swells as a result of the hydrophilic nature of the oxidized regenerated cellulose. The composition may also be exposed to an exogenous source of aqueous fluid, preferably sterile phosphate buffered saline, immediately prior to application so as to aid in delivering the composition. Other suitable aqueous solutions that may be used just prior to implantation include sterile forms of Ringers solution, saline, and dextrose solution. In certain of the forms described above, the flowability of the wet composition allows it to conform to irregularities, crevices, cracks, or holes in the tissue site.

The above described compositions may be used as medical devices. For example, when the oxidized regenerated cellulose is a fabric, the composition may be used as an adhesion barrier or a hemostatic wound dressing. Additionally, the composition may be used as a component of, for example, a hernia repair mesh or any other medical device. Specifically, the composition may form one layer of a multi-laminate hernia repair mesh. When the composition comprises oxidized regenerated cellulose particles and NSAID particles, the composition may be applied directly to a surgical wound site or trauma site, or may be suspended in a polymer solution and coated onto at least a portion of a medical device. Polymers that may be utilized to coat the medical devices include, but are not limited to, polysaccharides and proteins such as collagen and gelatin. Polysaccharides include, without limitation, cellulose, alkyl cellulose, e.g. methylcellulose, alkyl-hydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of medical devices that may be incorporated with the polymers above include, but are not limited to, sutures, textiles, catheters, cannulas, drains, meshes, staples, clips, or tissue augmentation/support/replacement prostheses. When the composition is a foam sponge, foam beads or agglomerates, the composition may be used directly at a surgical site or trauma site, for treatment of localized pain. Similarly, a medical device may be manufactured to incorporate the foam sponge, foam beads, fiber structures or agglomerates.

Several experiments were conducted to demonstrate the utility of the composition comprising oxidized regenerated cellulose and NSAID of the present invention in treating post-surgical pain. These experiments included an in vivo pharmacokinetic analysis of the release of diclofenac from the composition to surrounding tissues. In addition, an animal model designed specifically to study analgesic efficacy of compositions was utilized. The method of making the composition and methods required to demonstrate its therapeutic effect in treating post-surgical pain will now be described in detail.

EXAMPLES

Method of Preparing Samples

All samples of oxidized regenerated cellulose were prepared from Surgicel® Fibrillar absorbable hemostat, an oxidized regenerated cellulose product available from Johnson & Johnson Wound Management Worldwide, a division of Ethicon, Inc., Somerville, N.J., a Johnson & Johnson Company.

Example 1

Co-blended powders of oxidized regenerated cellulose and diclofenac sodium in an amount of approximately 20 mg oxidized regenerated cellulose powder per 1 mg diclofenac sodium powder, or a 20:1 oxidized regenerated cellulose powder to diclofenac sodium powder mass ratio. Other mass ratios of oxidized regenerated cellulose powder: diclofenac sodium powder have also been made in the range of 40:1 to 2:1. This corresponds to a concentration of non-steroidal anti-inflammatory drug in the composition of about 2.5 to 50 percent by weight, respectively. To achieve a range of oxidized regenerated cellulose particle sizes to be used in the co-blended powder, Surgicel Fibrillar™ samples were first frozen in liquid nitrogen. The frozen samples were then milled with a cryogenic mill.

The cryogenic milling process will now be described in detail. Approximately 0.5 grams of 2 cm×2 cm squares Surgicel Fibrillar™ was added to a steel cryo-tube. The cryo-tube was a stainless steel centered tube, which incorporated an internal metal impactor and was sealed at each end with stainless steel vial caps. The cryo-tube containing the oxidized regenerated cellulose was placed into the SPEX-6750-115 cryogenic mill, which is a cryogenic impact grinder with a self-contained liquid nitrogen tub and insulated case. When the lid was closed the charge loader containing the cryo-tube was immersed in liquid nitrogen. A pre-cool time of 4 minutes was programmed before the cryogenic milling process began. The cryogenic milling process time was set for 3.0 minutes, and the impact rate was set at 10 (two impacts per second). When the mill was activated, the metal agitator moved rapidly due to a fluctuating magnetic field produced by the machine and the contained material was processed into powder form. The material was collected in a clean glass jar and held under vacuum, between sample processes, to remove any residual moisture that may have collected on the powder.

The particle size of the milled material was determined by using a Beckman Coulter Particle Size Analyzer. The average particle size was found to be 20-25 microns. The material was shielded from any light source. The samples to be used in animal studies were transferred to a glass Wheaton vial, packaged in low temperature foil pouches and Cobalt sterilized (30 kGy). Samples were then stored in a cabinet purged with nitrogen gas at room temperature.

Example 2

Diclofenac sodium dry oxidized regenerated cellulose samples was prepared by soaking 1 cm×0.5 cm (≈5 mg) pieces of Interceed® absorbable adhesion barrier in diclofenac sodium aqueous solutions (5 mg/ml) at room temperature. After soaking for 30 minutes, the samples were taken out from the solution and dried first in open air and then in a vacuum oven at room temperature. Part of the diclofenac sodium/oxidized regenerated cellulose dry formulation samples was treated with cobalt radiation for sterilization. Before sterilization, drug loading was 11.3%, and after sterilization, it was 11.5%. This result indicates that the radiation sterilization did not significantly change the drug content of the formulation. FTIR analysis indicated there is no change chemically or structurally before and after sterilization.

Example 3

Animal Model to Assess Levels of Pain

In order to evaluate the analgesic efficacy of the composition containing oxidized regenerated cellulose particles dry blended with an NSAID powder (diclofenac sodium), the Brennan surgical pain model was used (Characterization of a rat model of incisional pain, Brennan, T. J., et al., Pain: 64 (1996); 493-501). The model was performed as follows. Male Sprague Dawley rats weighing 250-300 grams were used throughout the experiment. Prior to surgery, each animal was habituated to the testing environment and a baseline response to Semmes-Weinstein (von Frey) filaments was established. Animals were anesthetized using a fresh mixture of xylazine and ketamine containing 100 mg ketamine/ml and 20 mg xylazine/ml. Each animal was injected intramuscularly with 1 ml/kg to achieve surgical anesthesia. The left hind paw was aseptically prepared and a 1 cm incision through the skin and fascia was made on the plantar surface of the hind paw, extending from the ankle distally. The middle digital tendon was isolated and crushed using mosquito hemostats for 20 seconds. Following surgery animals were tested for mechanical sensitivity at 4, 24, 48, 72 and 96 hours following surgery.

Ten rats were evaluated in each of the following groups:

Group 1. Control group: all animals were given intraperitoneal (IP) injections of saline (1 ml/kg) 1 hour before testing for mechanical allodynia and hyperalgesia.

Group 2: Immediately post-tendon crush, the tendon was treated with a 6 mm×6 mm piece of oxidized regenerated cellulose (Surgicel® Fibrillar absorbable hemostat) that had 100 microliters of a saline solution containing Diclofenac sodium (10 mg/ml). This equates to a total of 1 mg of diclofenac sodium or approximately 4 mg/kg for a 250 g animal.

Group 3: Immediately post-tendon crush, a single dose (20 mg of micronized oxidized regenerated cellulose with an approximate particle size of 20-25 microns blended with 1 mg diclofenac sodium) was mixed with 100 microliters of a sterile saline solution. The composition was then applied to the site of the crushed tendon.

Group 4: Immediately post-tendon crush, the tendon was treated with a 6 mm×6 mm piece of oxidized regenerated cellulose (Surgicel® Fibrillar absorbable hemostat) that had 100 microliters of a saline solution containing Diclofenac sodium (5 mg/ml). This equates to a total of 0.5 mg of diclofenac sodium or approximately 2 mg/kg for a 250 g animal.

Comparative Example

Group 5: Immediately post-tendon crush, the tendon was treated with a 6 mm×6 mm piece of oxidized regenerated cellulose (Surgicel® Fibrillar absorbable hemostat) that had 100 microliters of a saline solution containing mepivacaine hydrochloride (10 mg/ml). This equates to a total of 1.0 mg of mepivacaine hydrochloride or approximately 4 mg/kg for a 250 g animal.

Comparative Example

Group 6: Immediately post-tendon crush, the tendon was treated with a 6 mm×6 mm piece of oxidized regenerated cellulose (Surgicel® Fibrillar absorbable hemostat) that had 100 microliters of a saline solution containing indomethacin (5 mg/ml). This equates to a total of 0.5 mg of indomethacin or approximately 2 mg/kg for a 250 g animal.

Comparative Example

Group 7: Immediately post-tendon crush, the tendon was treated with a 6 mm×6 mm piece of oxidized regenerated cellulose (Surgicel® Fibrillar absorbable hemostat) that had 100 microliters of a saline solution containing ketoprofen (5 mg/ml). This equates to a total of 0.5 mg of ketoprofen or approximately 2 mg/kg for a 250 g animal.

Comparative Example

Group 8: Immediately post-tendon crush, the tendon was treated with a 6 mm×6 mm piece of oxidized regenerated cellulose (Surgicel® Fibrillar absorbable hemostat) that had 100 microliters of a saline solution containing tramadol (20 mg/ml). This equates to a total of 2.0 mg of diclofenac sodium or approximately 8 mg/kg for a 250 g animal.

The pin-prick test was used to assess mechanical hyperalgesia. Briefly, a blunted safety pin was used to gently tent the plantar skin of each hind paw without breaking the skin. A stopwatch was used to measure the withdrawal time following this stimulus. Increased withdrawal time (in seconds) was interpreted as mechanical hyperalgesia.

Mechanical sensitivity or mechanical allodynia from each time point was normalized against the negative control group and against each individual animal's pre-surgical mechanical sensitivity. Mechanical sensitivity was assessed using a procedure described by Chaplan et al. (J. Neurosci. Methods 1994, 53: 55-63). A series of von Frey filaments of varying rigidity strength (typically eight filaments in the series) were applied to the plantar surface of the hind paw ipsilateral to the ligations with just enough force to bend the filament. The filaments were held in this position for no more than three seconds or until a positive allodynic response was displayed by the rat. A positive allodynic response consists of lifting the affected paw followed immediately by licking or shaking of the paw. The order and frequency with which the filaments were applied was determined using the Dixon up-down method. Testing was initiated with the middle filament of the series with subsequent filaments being applied in consecutive fashion, ascending or descending, depending on whether a negative or positive response, respectively, was obtained with the initial filament.

Figure 1:
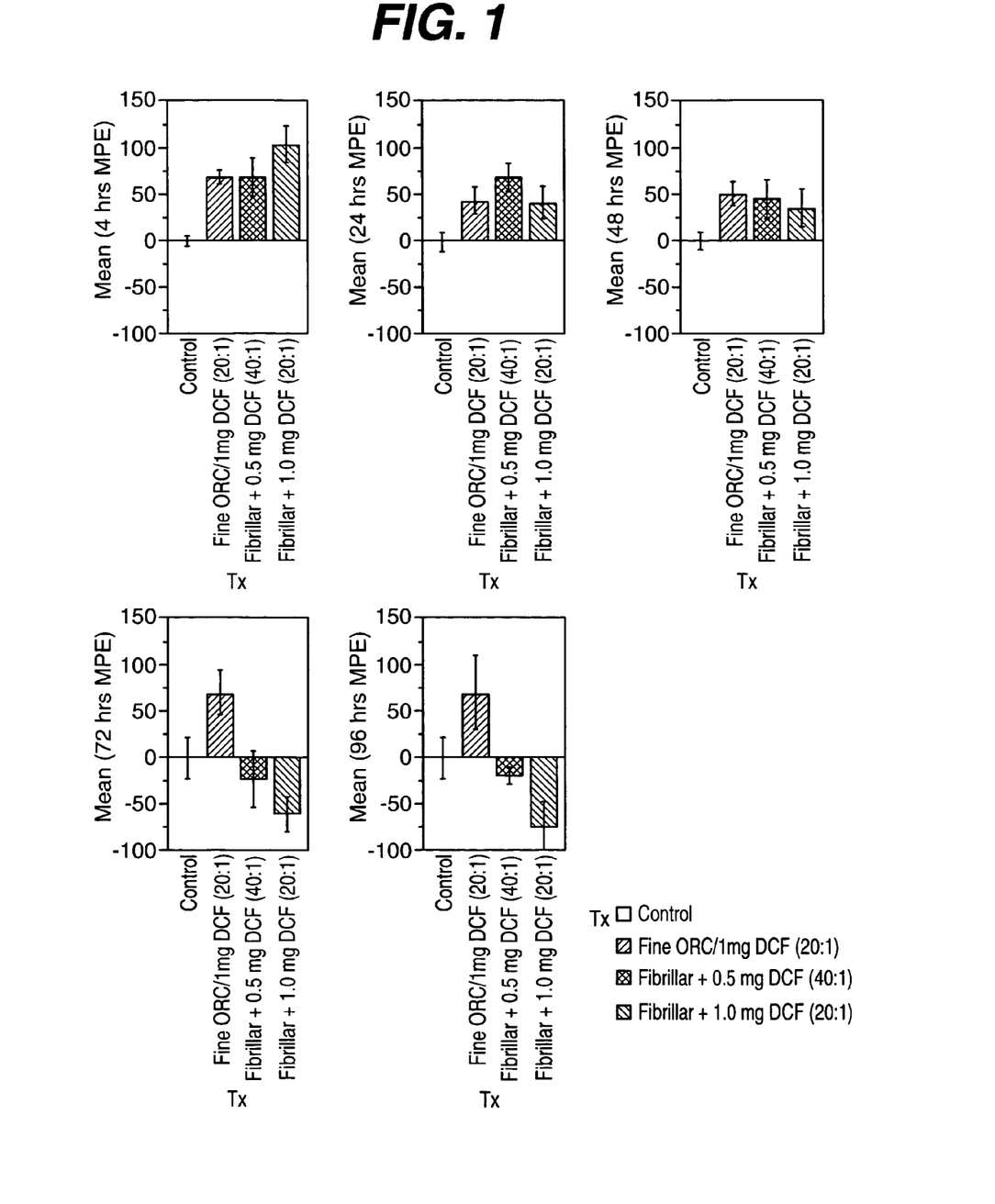
FIG. 1 illustrates the in vivo behavioral measurements of mechanical allodynia for various formulations of oxidized regenerated cellulose and diclofenac sodium.
Figure 2:
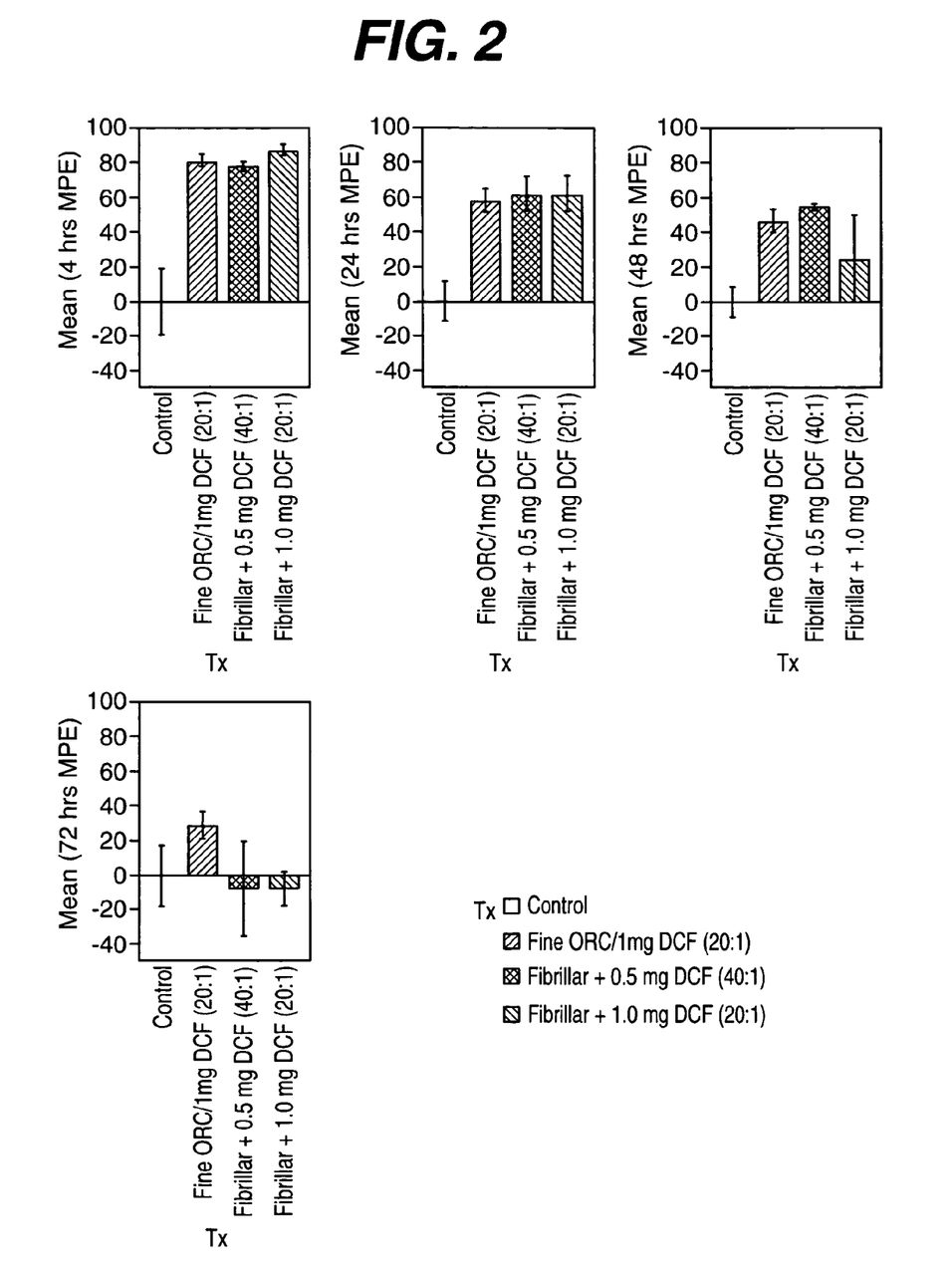
FIG. 2 illustrates the in vivo behavioral measurements of mechanical hyperalgesia for various formulations of oxidized regenerated cellulose and diclofenac sodium.

FIGS. 1 and 2 and Table 1 illustrate the mechanical allodynia and hyperalgesia response, and the efficacy determined by significant analgesia compared with control animals, respectively. Results are expressed as percent of Maximal Potential Efficacy (% MPE). The formula developed by Brady and Holtzman was used to calculate the % MPE, (Analgesic effects of intravenous morphine and enkephalins in non-dependent and morphine dependent rats. J. Pharmacol Exp. Ther. (1982), 222: 190-197). In this analysis, % MPE =100×[post-treatment mechanical threshold−pre-drug mechanical threshold]/[maximal mechanical threshold−pre-drug mechanical threshold]. Animal responses were normalized against the mean of the control group (vehicle only) and each animal's individual pre-surgical baseline. The scale for MPE reporting is not fixed. Results are reported in comparison to the negative control group and the pre-surgical response of the subjects. Negative values indicate behaviors that are worse than the untreated population and values greater than 100 represent a decrease in sensitivity to external stimuli beyond the pre-surgical response. An MPE value greater than 30 percent is considered efficacious/clinically effective. Results were analyzed using a computer based statistical package (JMP™ software). A non-paired t-test at each time point was used to identify changes from the control (vehicle treated) group.

The results presented in FIGS. 1 and 2 and Table 1 demonstrate that the composition of oxidized regenerated cellulose and diclofenac sodium is effective in the alleviation of post-surgical pain. The group of animals that received the 6 mm×6 mm samples of oxidized regenerated cellulose (Surgicel® Fibrillar absorbable hemostat) plus diclofenac sodium and saline provided analgesia for a period of 48 hours, with a smaller benefit at 72 hours. Micronized oxidized regenerated cellulose (approximately 20-25 micron average diameter) mixed with diclofenac sodium and saline and administered provided a significant increase in analgesic effect through 72 hours, with some effect at 96 hours.

Table 1. Efficacy of Composition of NSAIDS and Various Forms of Oxidized Regenerated Cellulose

TABLE 1

| | OXIDIZED REGENERATED CELLULOSE | | | | |
| --- | --- | --- | --- | --- | --- |
| | Micronized (20–25 um) | Surgicel® Fibrillar absorbable hemostat 6 × 6 mm | Interceed® absorbable adhesion barrier 6 × 6 mm | Intra-plantar injection | Repeated IPL injec. |
| DCF Sol'n 0.5 mg | | 48 Hrs effect | 48 Hrs effect | 4 Hrs effect | 4 Hrs effect |
| DCF Sol'n 1.0 mg | 72 Hrs effect | 48 Hrs effect | | | |
| Mepiv Sol'n 1.0 mg | | 4 Hrs effect | | 4 Hrs effect | 72+ Hrs effect |
| Inodmethacin Sol'n 0.5 mg | | Ineffective | | | |
| Ketoprofen Sol'n 0.5 mg | | Ineffective | | | |
| Tramadol Sol'n 2 mg | | 24 Hrs effect | | | |
| DCF dry 1 mg | 72 Hrs effect | | | | |
| DCF Free acid 1 mg powder | 72 Hrs effect | | | | |
| Mepiv powder 1.0 mg | Ineffective | | | | |

Example 3

Pharmacokinetic Evaluation

Pharmacokinetic studies in a rat model were conducted to determine the rate of diclofenac release from the composition. Male Sprague Dawley rats (four rats per time point per group) were anesthetized with isoflurane and subjected to a single surgical incision on the plantar surface of the left hind paw. The medial tendon was exposed by blunt dissection and subjected to a 20 second clamp using a mosquito hemostat.

In Group 1 the incision was sutured closed following manipulation of the tendon. The rats were administered an intraperitoneal injection of 5 mg/kg Diclofenac (as sodium salt, saline vehicle) 4 hours and 23 hours post-surgery. Blood and tissue samples were harvested at 0.25, 1, 4 and 6 hours after the second dose.

In Group 2, oxidized regenerated cellulose (Surgicel® Fibrillar absorbable hemostat) was implanted between the tendon and the metatarsals and 0.5 mg of Diclofenac (as sodium salt, saline vehicle) was instilled directly into the wound site and the incision was sutured closed. Blood samples were taken at 0.25,1, 4, 6, 24 and 48 hours post surgery.

Blood was harvested into K-EDTA tubes via cardiac puncture while the rats were anesthetized with isoflurane. Rats were terminated immediately after the blood draw by $CO_2$ inhalation, and the skin, muscle fascia and tendon of the left hind paw incision site were harvested. The contralateral tissue of the right hind paw was harvested and retained separately.

Blood samples were centrifuged to yield plasma, the resulting plasma as well as tissue samples were sent to Covance, Madison Wis. for LC/MS/MS analysis of diclofenac. Briefly, the analytical method involves extracting ~50 mg of tissue or 50 uL of plasma w/acetonitrile; the residue of the ACN extract is analyzed by tandem mass spectroscopy. The dynamic ranges of the plasma and tissue assays were 25 to 12,500 ng/mL and 25 to 12,500 ng/g, respectively.

Figure 3A:
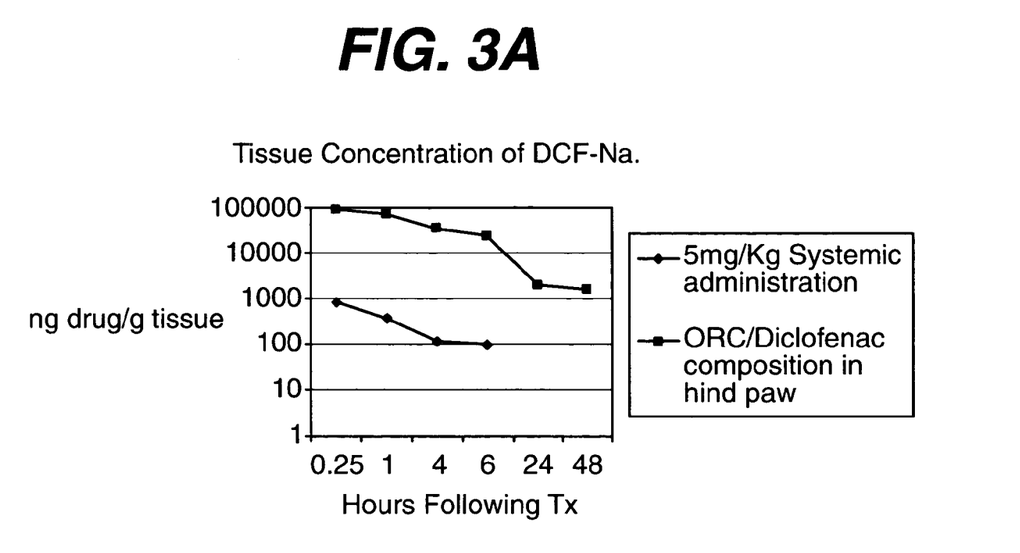
FIG. 3A illustrates diclofenac concentrations remaining relatively high in the surgical sites after local administration of a composition containing dry oxidized regenerated cellulose and diclofenac.
Figure 3B:
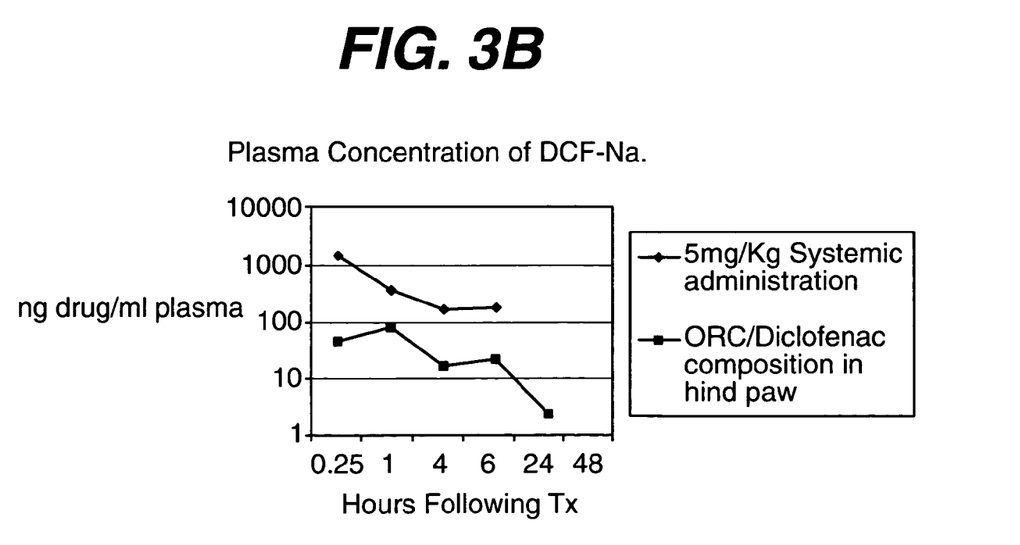
FIG. 3B illustrates how the local administration of diclofenac from the composition provides plasma concentrations of diclofenac that are much lower than that resulting from systemic administration.

The therapeutic benefit of the dry composition of oxidized regenerated cellulose particles and diclofenac sodium is illustrated in FIGS. 3A and 3B. FIG. 3A demonstrates how diclofenac concentrations at the surgical site remained relatively high after the local administration of a composition containing oxidized regenerated cellulose and diclofenac. This is in contrast to the rapid decline in tissue concentrations of diclofenac observed with the intraperitoneal injection of diclofenac solution. FIG. 3B illustrates how the local administration of diclofenac from the composition provides plasma concentrations of diclofenac that are much lower than that resulting from systemic administration. Thus, any reduction in analgesia can be attributed primarily to the local delivery of diclofenac from the composition.

Example 4

Carboxymethyl Cellulose (CMC)/Oxidized Regenerated Cellulose/Diclofenac-Sodium (DFNA) Foams In this experiment, 1% Na—CMC aqueous solution was prepared by mixing 1 g of Na—CMC dry powders into 100 mL water. The solution was stirred by magnetic stir. The uniform transparent solution was made after a few hours. About 25 g of 1% Na—CMC solution was added to a glass vial. Surgicel® Fibrillar absorbable hemostat was cryogenic milled to particles using Spex Mill. The average size of the oxidized regenerated cellulose particles was about 25 micron. Then, about 3 g of oxidized regenerated cellulose particles were added into the Na—CMC solution. After that, about 0.3 g of diclofenac sodium particles was added to the carboxymethyl cellulose-oxidized regenerated cellulose solution. The carboxymethyl cellulose-oxidized regenerated cellulose-diclofenac sodium mix was then homogenized for about 2 minutes until it was uniform. The homogenized solution was then poured into two 4×7 molds. The mold was then put into the freeze dryer, preset at −20° C. The solution was frozen within a few minutes. The freeze-drying program was run so that the water is freeze-dried for 12 to 24 hours and a carboxymethyl cellulose—oxidized regenerated cellulose-diclofenac sodium foam was made. Based on the in vivo result of Examples 2 and 3, this composition is expected to exhibit the same therapeutic effect.

In-vitro drug release testing was conducted in a shaker water bath maintained at 37° C. and agitated 30 cpm. Polymer films (1 cm×1 cm) loaded with the appropriate active agent were placed in 20 ml glass scintillation vials filled with 20 mls of 0.01 M phosphate buffer solution (pH 7.4) and sealed with a screw cap. Buffer solution aliquots were collected at designated time intervals (3, 12, 24, 36, 48 and 72 hours). The amounts of active agent released into the buffer solution were measured using a HPLC method as described below.

HPLC assay for diclofenac sodium salt is conducted as follows. First, a phosphate buffer with a pH 2.5 is made by mixing an equal volume of 0.01 M phosphoric acid and 0.01 M monobasic sodium phosphate and adjusting the pH to 2.5 with additional portions of the appropriate component.

The mobile phase was prepared by mixing methanol and pH 2.5 phosphate buffer in ratio of 70:30. The standard solutions was prepared by dissolving about 50 mg of diclofenac sodium reference standard in approximately 40.0 mL of MeOH, using sonication if necessary, in a 50 mL volumetric flask (brought to volume with methanol). Then the standard stock solution was diluted with diluents (70:30 MeOH:water) to desired concentrations. The HPLC conditions were:

| | |
|---|---|
| Column: | Phenomenex Luna C18, 150 mm × 4.6 mm, 5μ |
| Mobile phase: | MeOH: phosphate buffer 70:30 |
| Flow rate: | 1 mL/min |
| Detection: | UV 254 nm |
| Injection Volume: | 10 μL |
| Run Time: | 15 min |

Figure 4:
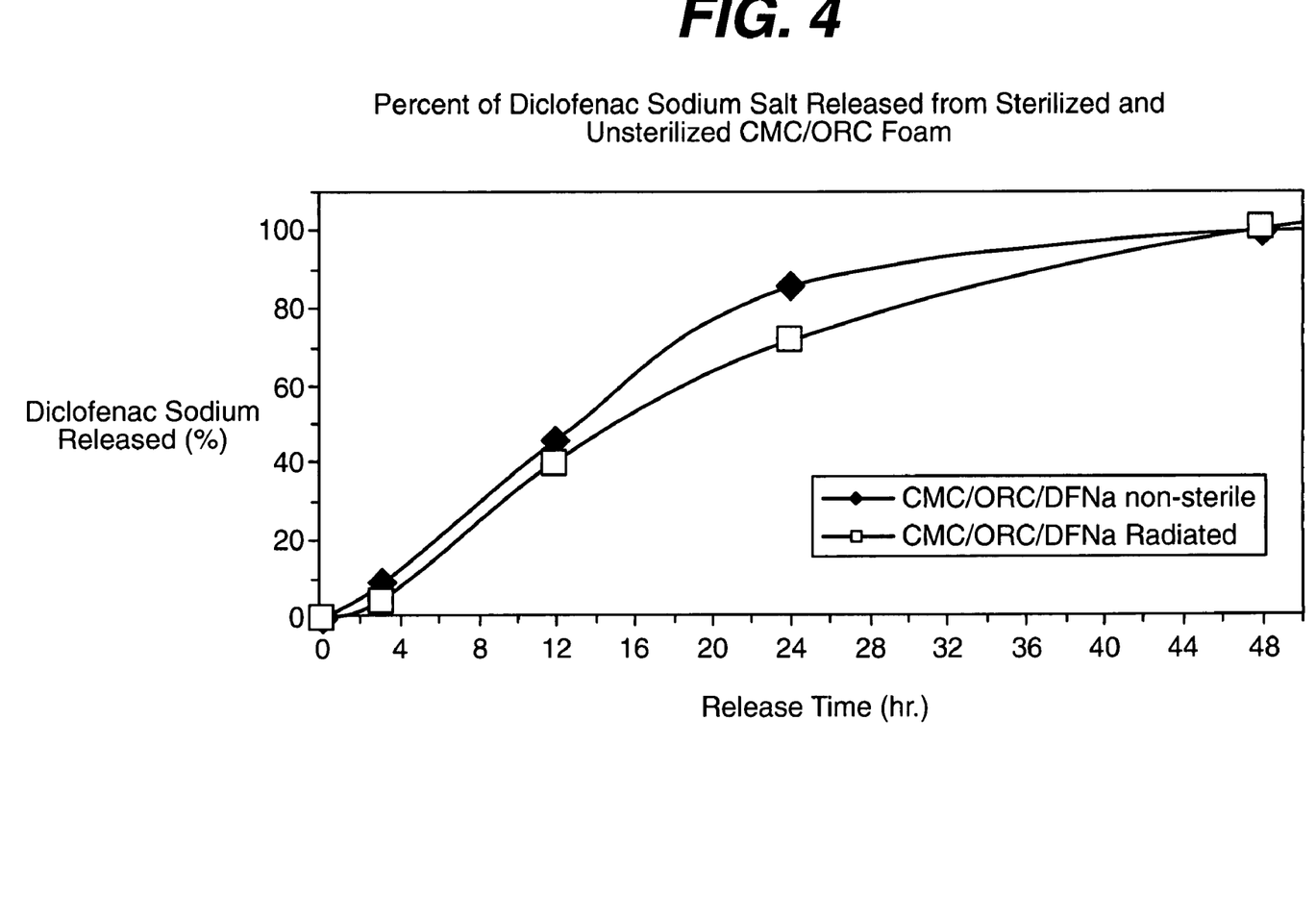
FIG. 4 illustrates in vitro release of Diclofenac Sodium (DFNa) from Carboxymethyl Cellulose—Oxidized Regenerated Cellulose—DFNa foams

The data generated and release profiles are summarized in FIG. 4. It was found that there was no significant difference in the release rate before and after cobalt sterilization.

It should be noted that gamma irradiated foams dissolved in PBS buffer after 12 hours and non-sterile samples dissolved in PBS after 2~3 days. It should also be noted that the carboxymethyl cellulose foam alone would be dissolving into PBS within a couple minutes resulting in complete drug burst. As shown in FIG. 4, the carboxymethyl cellulose-oxidized regenerated cellulose diclofenac sodium foam can provide greater than 48 hours of controlled release. Based on the in vivo result of Examples 2 and 3, this composition is expected to exhibit the same therapeutic effect. In addition, the carboxymethyl cellulose foam remained as a soft and flexible foam for a half day before it gels and dissolves in PBS making it an ideal carrier for delivering oxidized regenerated cellulose—diclofenac sodium particle formulations either directly into the targeted area or attached to an existing device such as hernia mesh.

While there has been shown and described what is considered to be preferred embodiments of the invention, it will, of course, be understood that various modifications and changes in composition could readily be made without departing from the spirit of the invention. It is therefore intended that the invention be not limited to the exact compositions described and illustrated, but should be constructed to cover all modifications that may fall within the scope of the appended claims.

What is claimed is:

1. A composition for reducing pain administered non-systematically and intercorporeally at a surgical wound site or trauma site comprising oxidized regenerated cellulose and a non-steroidal anti-inflammatory drug or pharmaceutically acceptable salt or ester thereof, where the non-steroidal anti-inflammatory drug is an acid having a secondary amine group.

2. The composition of claim 1, wherein the non-steroidal anti-inflammatory drug is selected from the group consisting of diclofenac or mefenamic acid.

3. The composition of claim 1, wherein the non-steroidal anti-inflammatory drug is diclofenac or a pharmaceutically acceptable salt thereof.

4. The composition of claim 1, wherein the concentration of non-steroidal anti-inflammatory drug in the composition is about 0.25 to 50 percent by weight based on the weight of the oxidized regenerated cellulose.

5. The composition of claim 1, wherein the non-steroidal anti-inflammatory drug or pharmaceutically acceptable salt or ester thereof is present in an effective amount to treat localized pain.

6. The composition of claim 1, wherein the composition is in the form of a textile, particles, a foam sponge, foam beads, or agglomerates.

7. The composition of claim 6, wherein the textile comprises an oxidized regenerated cellulose textile and the non-steroidal anti-inflammatory drug or a pharmaceutically acceptable salt or ester thereof is incorporated into the composition by (a) dip coating the oxidized regenerated cellulose textile in a solution or suspension of the non-steroidal anti-inflammatory drug; (b) spray drying a solution or suspension of the non-steroidal anti-inflammatory drug onto the oxidized regenerated cellulose textile; (c) laminating at least one polymer film formed from a solution or suspension of the non-steroidal anti-inflammatory drug onto the oxidized regenerated cellulose textile; or (d) forming a microporous polymeric matrix of non-steroidal anti-inflammatory drug onto the oxidized regenerated cellulose textile.

8. The composition of claim 7, wherein the polymer film comprises a polymer selected from the group consisting of poly(acrylic acid), hydroxylpropyl methyl cellulose, polyvinyl pyrrolidone, polyethylene glycol, and polyethylene oxide.

9. The composition of claim 6, wherein the particles are comprised of oxidized regenerated particles having an average particles size of 1-1000 microns, and non-steroidal anti-inflammatory drug particles or a pharmaceutically acceptable salt or ester thereof.

10. The composition of claim 6, wherein the particles are comprised of oxidized regenerated particles having an average size of 20-25 microns, and non-steroidal anti-inflammatory drug particles or a pharmaceutically acceptable salt or ester thereof.

11. The composition of claim 6, further comprising a binder component when the composition is in the form of a foam sponge, foam beads or agglomerates.

12. The composition of claim 11, wherein the binder component is at least one polysaccharide selected from the group consisting of cellulose, alkyl cellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives thereof.

13. The composition of claim 11, wherein the oxidized regenerated cellulose is in the form of particles or short fibers having an average size ranging from about 500 to about 5000 microns.

14. The composition of claim 1, wherein the composition further comprises an anesthetic or an atypical opiate.

15. The composition of claim 14, wherein the anesthetic is selected from the group consisting of mepivacaine, bupivicaine, procaine, lidocaine, and ropivacaine; and the atypical opiate is loperamide or tramadol.

16. A medical device comprising the composition of composition of claim 1.

17. The medical device of claim 16, wherein the medical device is a suture, textile, catheter, cannula, mesh, drain, clip, staple or tissue augmentation/support/replacement prostheses.

18. A method for reducing localized pain at a surgical wound site or trauma site comprising applying to the site an effective amount of the composition according to claim 1 where the non-steroidal anti-inflammatory drug is an acid having a secondary amine group.

19. The method of claim 18, wherein the non-steroidal anti-inflammatory drug is diclofenac or a pharmaceutically acceptable salt thereof.

20. A method for reducing localized pain at a surgical wound site or trauma site comprising the steps of (i) applying to the site an oxidized regenerated cellulose and (ii) applying to the site an effective amount of a non-steroidal anti-inflammatory drug or pharmaceutically acceptable salt or ester thereof to treat the localized pain, where the non-steroidal anti-inflammatory drug is an acid having a secondary amine group.

21. The method of claim 20, wherein the non-steroidal anti-inflammatory drug is diclofenac or a pharmaceutically acceptable salt thereof.

* * * * *